United States Patent

Sternberg et al.

[11] Patent Number: 6,032,807
[45] Date of Patent: Mar. 7, 2000

[54] METHODS FOR CORRELATING AVERAGE FIBER DIAMETER WITH PERFORMANCE IN COMPLEX FILTRATION MEDIA

[75] Inventors: Shmuel Sternberg, Northbrook; Daniel R. Lynn, Springe Grove, both of Ill.

[73] Assignee: Baxter International Inc., Deerfield, Ill.

[21] Appl. No.: 08/697,270

[22] Filed: Aug. 21, 1996

Related U.S. Application Data

[63] Continuation of application No. 08/558,458, Nov. 16, 1995, abandoned, which is a continuation of application No. 08/392,297, Feb. 22, 1995, abandoned, which is a continuation of application No. 08/173,608, Dec. 22, 1993, abandoned.

[51] Int. Cl.$^7$ .............................. B01D 24/10; B01D 39/08
[52] U.S. Cl. .......................... 210/491; 210/488; 210/490; 210/507; 210/508; 73/159; 264/258; 264/DIG. 26; 264/DIG. 48
[58] Field of Search ..................................... 210/483, 488, 210/489, 491, 496, 505, 507, 508, 509, 490; 428/212, 213, 218, 220, 311.51, 315.9, 332; 73/159, 160; 264/DIG. 48, DIG. 26, 258

[56] References Cited

U.S. PATENT DOCUMENTS

| | | | |
|---|---|---|---|
| 4,157,967 | 6/1979 | Meyst et al. | 210/489 |
| 4,330,410 | 5/1982 | Takenaka et al. | 210/676 |
| 4,701,267 | 10/1987 | Watanabe et al. | 210/806 |
| 5,152,905 | 10/1992 | Pall et al. | 210/767 |
| 5,186,843 | 2/1993 | Baumgardner et al. | 210/505 |
| 5,190,657 | 3/1993 | Heagle et al. | 210/505 |
| 5,290,449 | 3/1994 | Heagle et al. | 210/505 |
| 5,298,165 | 3/1994 | Oka et al. | 210/645 |
| 5,591,337 | 1/1997 | Lynn et al. | 210/489 |

FOREIGN PATENT DOCUMENTS 2908722  9/1979  Germany.

*Primary Examiner*—John Kim
*Attorney, Agent, or Firm*—Daniel D. Ryan; Denise M. Serewicz; Bradford R. L. Price

[57] ABSTRACT

A method correlates average fiber diameter with performance for a complex filtration media comprising a matrix of fibers having a fibrillated component with a diameter so small (e.g., less than 0.01 microns), that cannot be physically measured with accuracy. The method manufactures a selected matrix, derives the number average diameter of the fibers according to prescribed steps, some of which do not require actual physical measurements, and observes a performance characteristic. The method repeats the foregoing steps for different matrixes, yielding different number average diameters. The method expresses change in the selected performance characteristic as a function of change in number average diameter of the matrices.

5 Claims, 9 Drawing Sheets

FIG.6
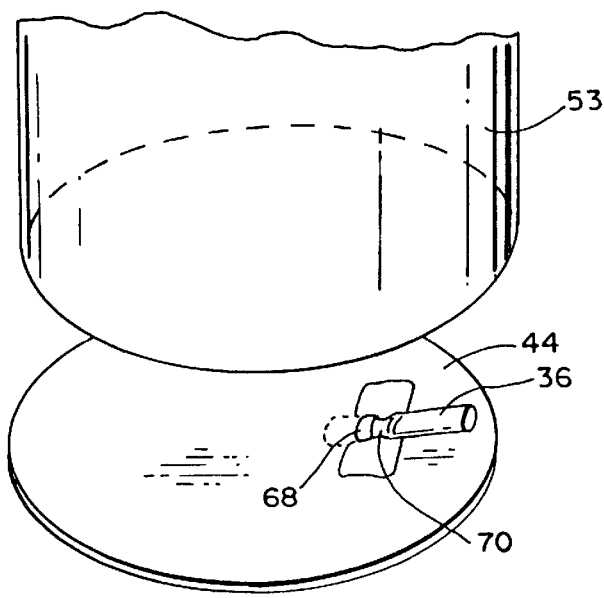
FIG.6A
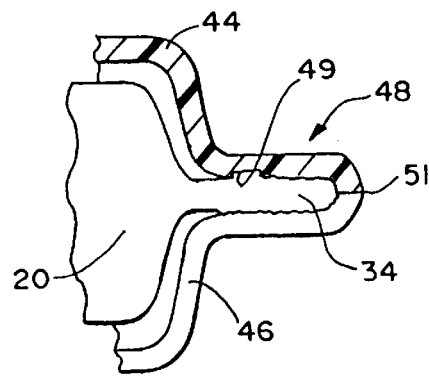
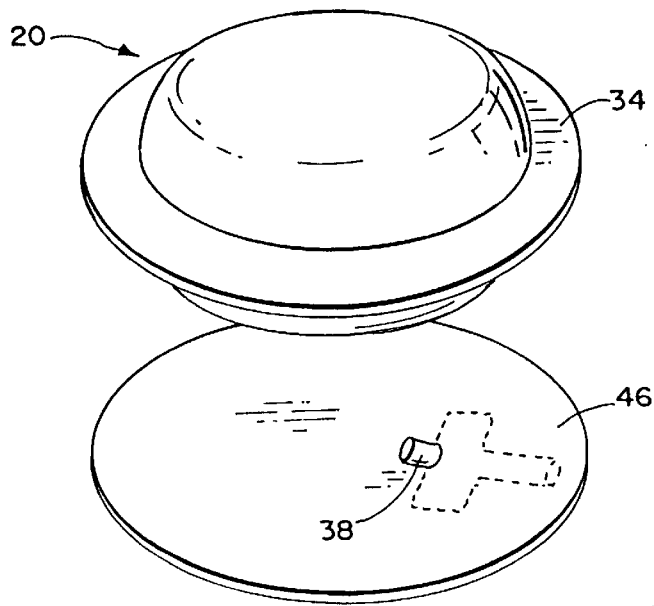
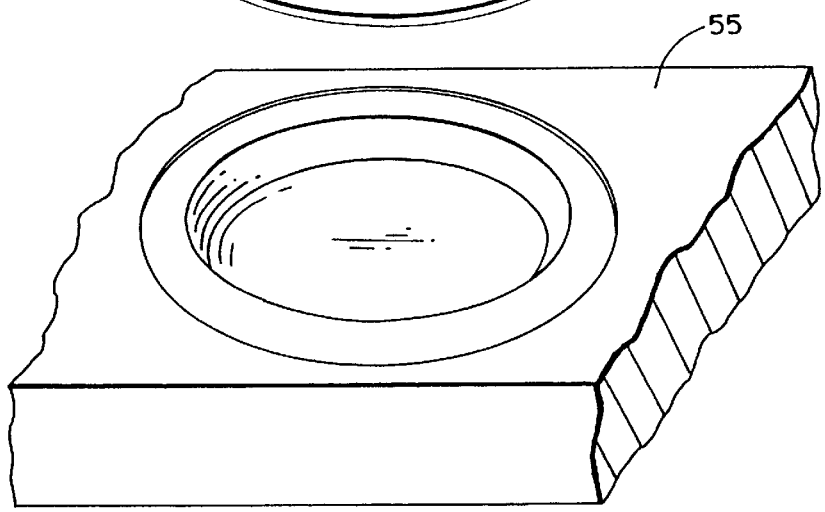

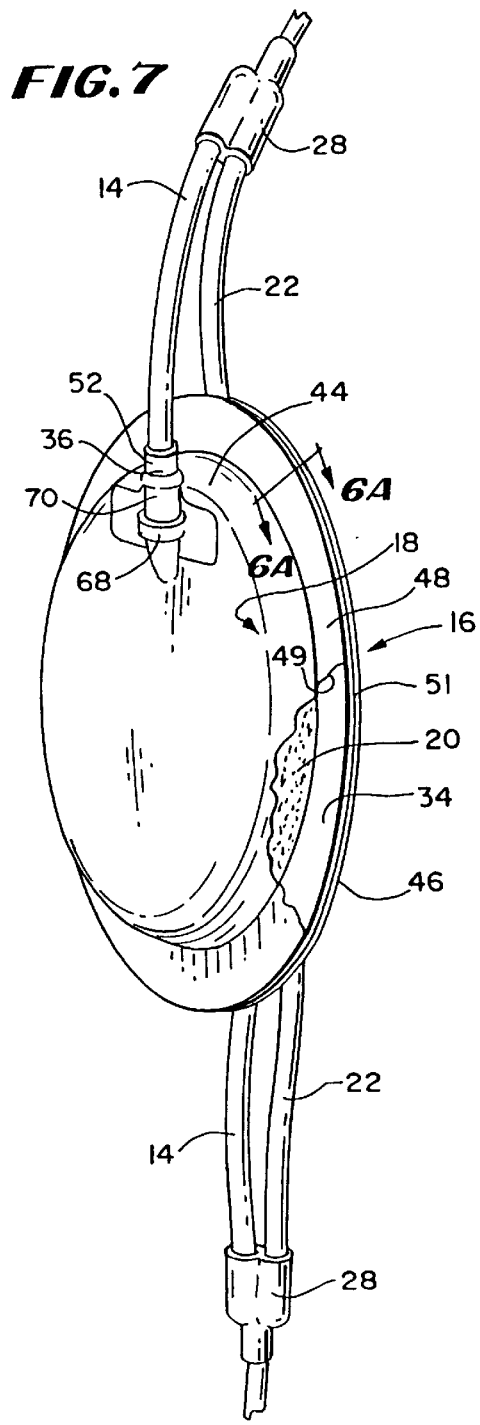
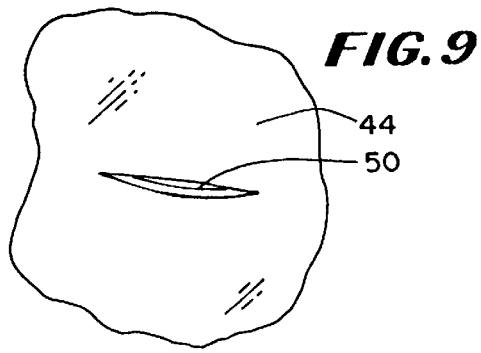
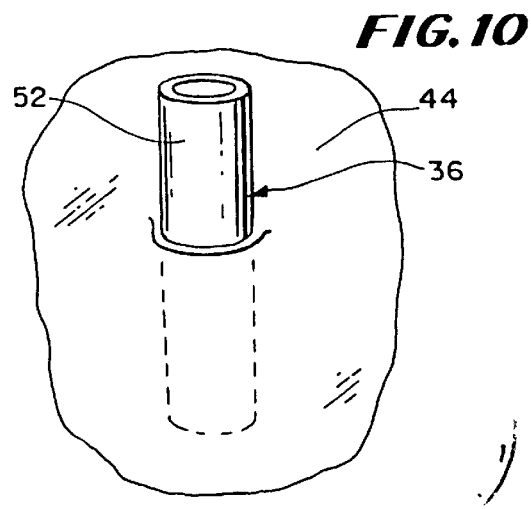
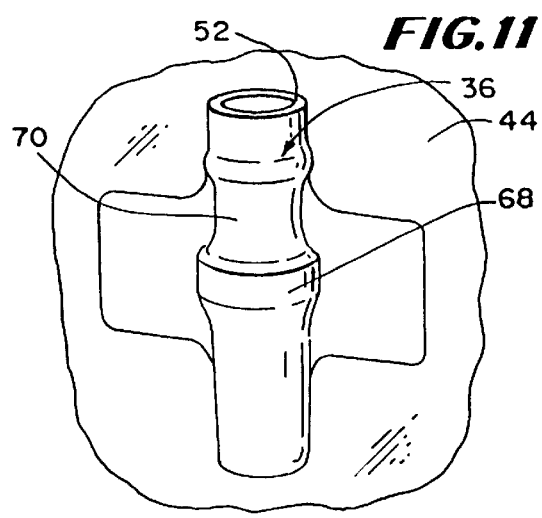
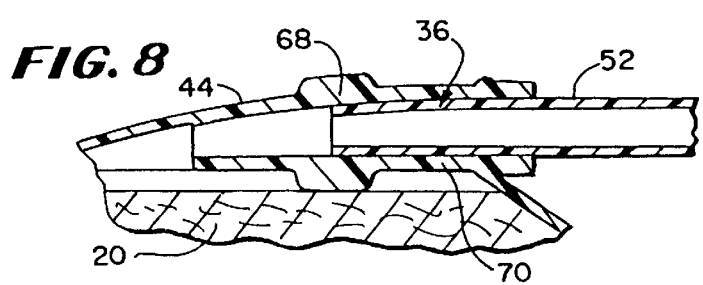

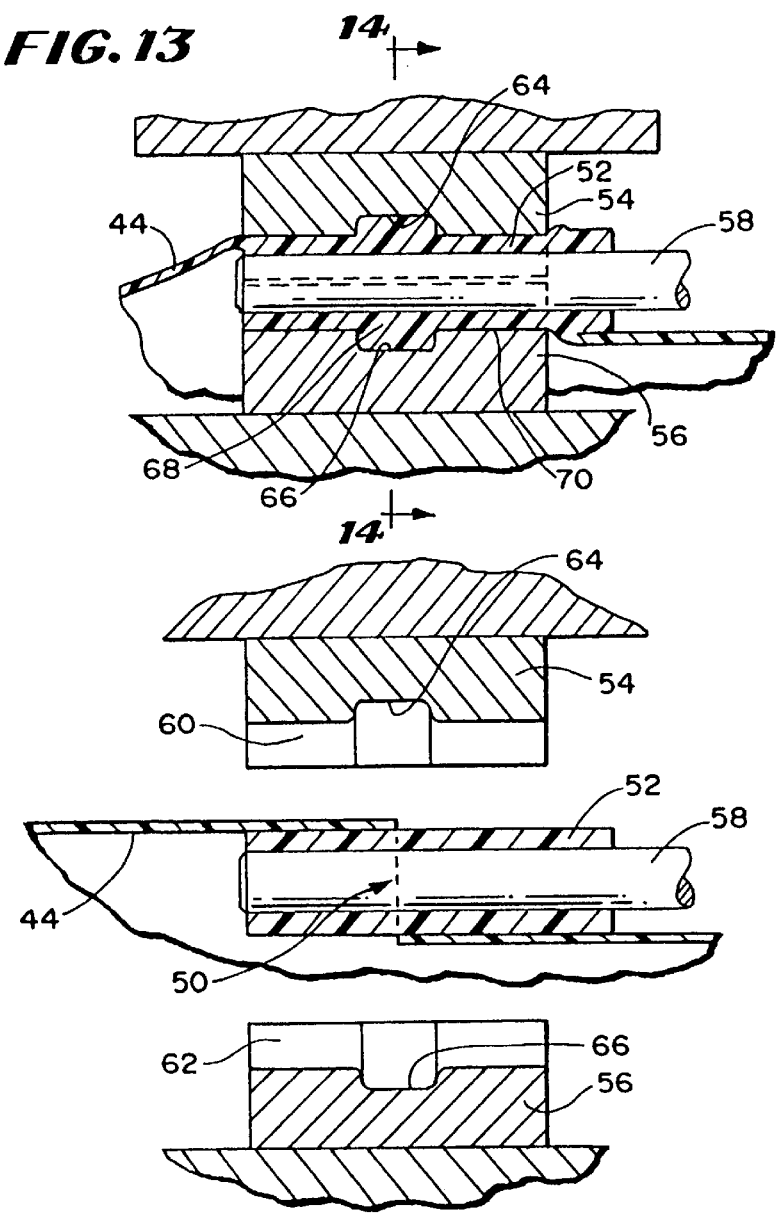
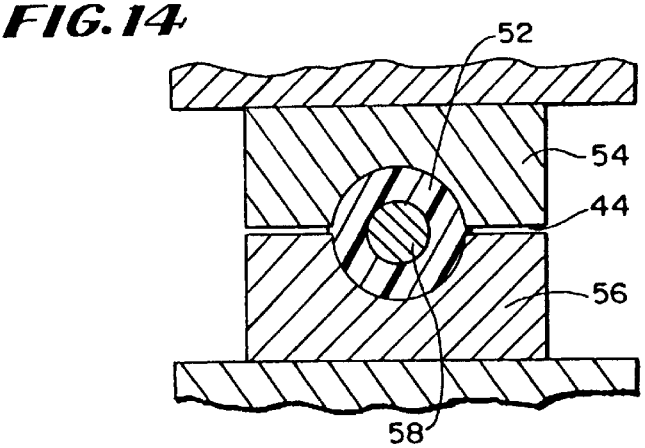

FIG. 15

|  | WEIGHT PERCENTAGE OF FIBERGLASS | | | | | |
|---|---|---|---|---|---|---|
| WEIGHT PERCENTAGE OF CELLULOSE ACETATE | 1.00% | 5.00% | 10.00% | 15.00% | 20.00% | 25.00% |
| 1.00% | 0.378 | 0.398 | 0.418 | 0.434 | 0.447 | 0.458 |
| 2.00% | 0.269 | 0.286 | 0.304 | 0.320 | 0.335 | 0.348 |
| 3.00% | 0.231 | 0.244 | 0.259 | 0.272 | 0.285 | 0.296 |
| 4.00% | 0.212 | 0.222 | 0.235 | 0.246 | 0.256 | 0.266 |
| 5.00% | 0.201 | 0.209 | 0.219 | 0.229 | 0.238 | 0.247 |
| 6.00% | 0.193 | 0.200 | 0.209 | 0.217 | 0.225 | 0.233 |
| 7.00% | 0.187 | 0.194 | 0.202 | 0.209 | 0.216 | 0.223 |
| 8.00% | 0.183 | 0.189 | 0.196 | 0.202 | 0.209 | 0.215 |
| 9.00% | 0.180 | 0.185 | 0.191 | 0.197 | 0.203 | 0.209 |
| 10.00% | 0.177 | 0.182 | 0.188 | 0.193 | 0.199 | 0.204 |

METHODS FOR CORRELATING AVERAGE FIBER DIAMETER WITH PERFORMANCE IN COMPLEX FILTRATION MEDIA

This is a continuation of application Ser. No. 08/558,458 filed Nov. 16, 1995, abandoned; which is a continuation of application Ser. No. 08/392,297 filed Feb. 22, 1995, abandoned; which is a continuation of application Ser. No. 08/173,608 filed Dec. 22, 1993, abandoned.

FIELD OF THE INVENTION

The invention generally relates to blood collection and processing systems and methods. In a more particular sense, the invention relates to systems and methods for removing leukocytes from red blood cells before transfusion or long term storage.

BACKGROUND OF THE INVENTION

Most of the whole blood collected from donors today is not itself stored and used for transfusion. Instead, the whole blood is separated into its clinically proven components (typically red blood cells, platelets, and plasma), which are themselves individually stored and used to treat a multiplicity of specific conditions and diseased states. For example, the red blood cell component is used to treat anemia; the concentrated platelet component is used to control thrombocytopenic bleeding; and the platelet-poor plasma component is used as a volume expander or as a source of Clotting Factor VIII for the treatment of hemophilia.

Plastic bags have met widespread use and acceptance for collecting, processing and storing these blood components.

In collecting whole blood components for transfusion, it is desirable to minimize the presence of impurities or other materials that may cause undesired side effects in the recipient. For example, because of possible febrile reactions, it is generally considered desirable to transfuse red blood cells substantially free of leukocytes, particularly for recipients who undergo frequent transfusions.

One way to remove leukocytes is by washing the red blood cells with saline. This technique is time consuming and inefficient, as it can reduce the number of red blood cells available for transfusion.

Another way to remove leukocytes is by filtration. Systems and methods for accomplishing this in conventional blood bag systems are described in Wisdom U.S. Pat. Nos. 4,596,657 and 4,767,541, as well as in Carmen et al U.S. Pat. Nos. 4,810,378 and 4,855,063. Other systems and methods for removing leukocytes in the blood bag systems are described in Stewart U.S. Pat. No. 4,997,577 and Stewart et al. U.S. Pat. No. 5,128,048. In these arrangements, an in line filtration device is used.

A need still exists for further improved systems and methods for removing undesired matter like leukocytes from blood components before transfusion or storage.

SUMMARY OF THE INVENTION

The invention provides a filtration media for removing leukocytes from a blood suspension. The media comprises non-contiguous layers having an overall thickness of greater than about 6 mm but not more than about 10 mm. Each non-contiguous layer comprises an interlocked matrix of polyester fibers, fiberglass fibers, and cellulose acetate fibrets. The matrix has a number average fiber diameter no greater than about 0.23 micron.

According to this aspect of the invention, the number average diameter is calculated as follows:

(i) deriving the length of each fiber material present in the matrix, using the following equation:

$$L_i = \frac{4Q_i}{\pi \rho_i d_i^2}$$

where:
$i$ is the selected fiber (polyester, fiberglass, and cellulose acetate fibrets);
$L_i$ is the length of the selected fiber (in cm);
$Q_i$ is the weight fraction of the selected fiber (expressed as a decimal; e.g., 10%=0.1);
$\pi$ is 3.1417;
$d_i$ is the diameter of the selected fiber (in cm); and
$\rho_i$ is the density of the selected fiber (in g/cm$^3$); and where:
the diameter of the cellulose acetate fibrets (which presents a complex fiber structure that cannot be readily measured by conventional means) is derived according to the following equation:

$$d = \frac{4}{\rho} \times \frac{1}{A/W}$$

where:
d is the diameter of the cellulose acetate fibrets (in cm, or, by multiplying cm by 10,000, in microns);
$\rho$ is the density of the cellulose acetate from which the fibrets are formed (in g/cm$^3$); and
A/W is the area-to-weight ratio of the cellulose acetate fibrets (in cm$^2$/g); and (ii) deriving the number average diameter of all fibers present in the matrix by adding together the product of the length $L_i$ (expressed in cm) and diameter divided by the length $L_i$ (in cm/g) for each fiber, using the following equation:

$$\frac{\Sigma L_i \times d_i}{\Sigma L_i}$$

where:
i is the fiber;
$L_i$ is the length of the fiber (in cm);
$d_i$ is the diameter of the fiber (in cm).

It has been determined that the number average fiber diameter, as calculated above, can be used to correlated various physical and performance characteristics of the complex leukodepletion media. A number average fiber diameter of no more than about 0.23 micron, as calculated above, correlates with an acceptable log reduction of leukocytes in whole blood at an acceptable whole blood flow rate.

Other features and advantages of the invention will become apparent upon review of the following description, drawings, and appended claims.

BRIEF DESCRIPTION OF THE DRAWINGS

FIGS. 6 and 6A are an exploded perspective view of the assembly of the filter housing to the composite filter pad assembly using a radiofrequency welding tool;

FIG. 7 is a perspective view of the filter device that is formed in FIG. 6;

FIG. 8 is a fragmentary cross-sectional view taken centrally through a port in the wall of the filter device of FIG. 7;

FIG. 9 is a fragmentary view of sheet of material showing an initial step in the manufacture of the port shown in FIG. 8;

FIG. 10 is a fragmentary view showing a further step in the manufacturing of the port shown in FIG. 8;

FIG. 11 is a fragmentary view showing the finished port in the filter device;

FIG. 12 is a central sectional view showing the components in the manufacture of the port prior to heating thereof;

FIG. 13 is a sectional view of the components shown in FIG. 12 during the heating step;

FIG. 14 is a sectional view taken along line 14—14 of FIG. 13;

FIG. 15 is a table, calculated according to one aspect of the invention, showing the number average fiber diameters for complex filtration media comprising given weight percentages of polyester fiber/core sheath; fiberglass fiber; and cellulose acetate fibrets;

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

Figure 1:
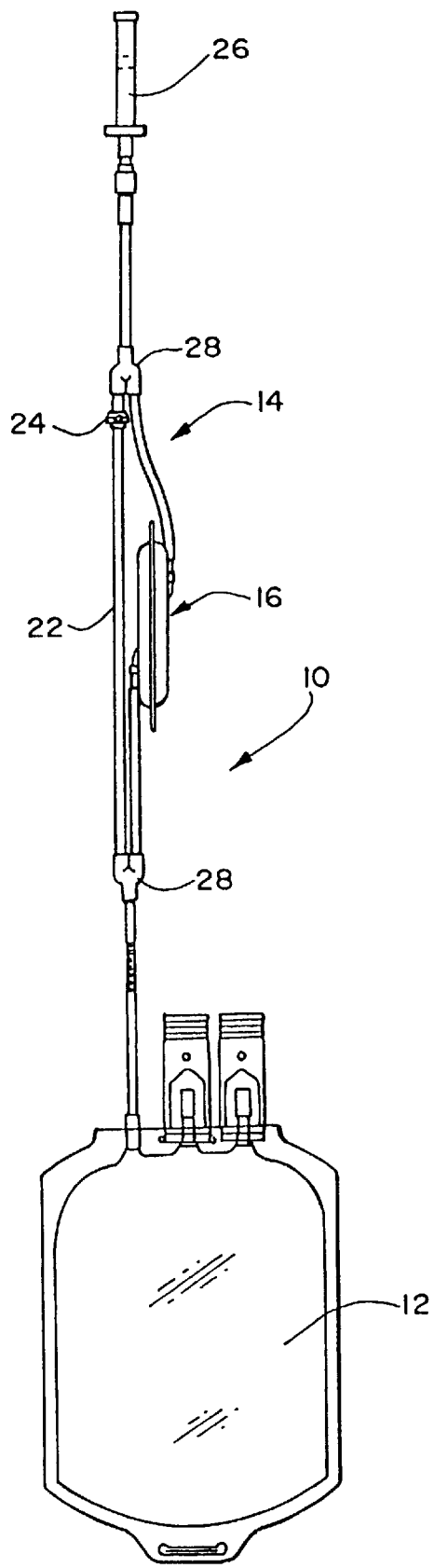
FIG. 1 is a schematic view of a blood collection assembly that embodies the features of the invention.

A blood collection assembly 10 is shown in FIG. 1. In the illustrated embodiment, the assembly 10 serves to filter leukocytes from red blood cells before transfusion.

In the embodiment shown in FIG. 1, the assembly 10 includes a transfer bag or container 12. The transfer bag 12 includes integrally attached transfer tubing 14. In the illustrated embodiment, the tubing 14 carries a conventional blood bag spike 26 at its distal end. As will be discussed later, other types of aseptic or sterile connectors can be used.

The transfer tubing 14 also carries an in line filter device 16. As FIGS. 2 and 7 best show, the filter device 16 includes a two part housing 18 that encapsulates a filter pad assembly 20. The pad assembly 20 is intended to be used to remove leukocytes from red blood cells.

The system 10 further includes a vent path 22. The vent path 22 also leads to the transfer bag 12, but it bypasses the filter device 16.

The vent path 22 includes an in line one way valve 24. The valve 24 allows flow through the path 22 from the transfer bag 12 toward the spike 26, but blocks flow through the path 22 from the spike 26 toward the transfer bag 12.

The bag 12 and tubing 14/22 associated with the assembly 10 can be made from conventional approved medical grade plastic materials, such as polyvinyl chloride plasticized with di-2-ethylhexyl-phthalate (DEHP). Conventional "Y" or "T" connectors 28 can be used to form the branched paths 14/22.

In use, the spike 26 is inserted into a port of a conventional primary blood collection bag (not shown). The primary bag contains red blood cells, which have been earlier separated from whole blood by centrifugation.

The red blood cells flow by gravity from the primary bag into the transfer tubing 14 and through the filter device 16. The filter pad assembly 20 removes leukocytes from the red blood cells as they pass through the device 16.

The one way valve 24 prevents parallel flow through the vent path 22.

The red blood cells, with all or a portion of the leukocytes removed, exit the filter device 16 and enter the transfer bag 12.

Once the primary bag connected to the spike 26 empties and flow has stopped, the user clamps the transfer tubing 14 immediately above and below the filter device 16. The user then manually squeezes the transfer bag 12 to express air from it. The air flows through the vent path 22, bypassing the filtration device 16, back toward the primary bag 16.

The user then removes the clamps above and below the filter device 16. The air pressure now resident in the assembly 10 upstream of the filter device 16 urges residual red blood cells through the filter device 16 and into the transfer bag 12.

The transfer bag 12 can now be detached from the assembly 10 for storing or transfusing the leukocyte-depleted red blood cells.

The detachment can be accomplished using a conventional heat sealing device (for example, the Hematron® dielectric sealer sold by Baxter Healthcare Corporation), which forms a hermetic, snap-apart seal in the transfer tubing 14 somewhere downstream of its junction with the vent path 22.

In an alternative arrangement (not shown), instead of the spike 26, the transfer tubing 14 can carry a sterile connection device that mates with a sterile connection device carried by the primary bag. The user brings the mating sterile connection devices together at time of use. Sterile connection devices that could be used for this purpose are shown in Granzow et al. U.S. Pat. Nos. 4,157,723 and 4,265,280.

Alternatively, the sterile connection can be accomplished in the manner described in Spencer U.S. Pat. No. 4,412,835. In this arrangement, a seal is formed between a region of the transfer tubing 14 and a tube carried by the primary bag.

Further details of the filter device 16 will now be discussed.

The Filtration Device

The filter device 16 can be variously constructed.

In the illustrated and preferred embodiment (best shown in FIGS. 2 and 7), the outer housing 18 enclosing the filter pad assembly 20 comprises two sheets 44 and 46 of flexible plastic material. The housing 18 is thus "soft," instead of rigid.

Also in the illustrated and preferred embodiment, the filter device 16 includes tangential side ports, one port 36 (in sheet 44) serving as an inlet and the other port 38 (in sheet 46) serving as an outlet.

Figure 2:
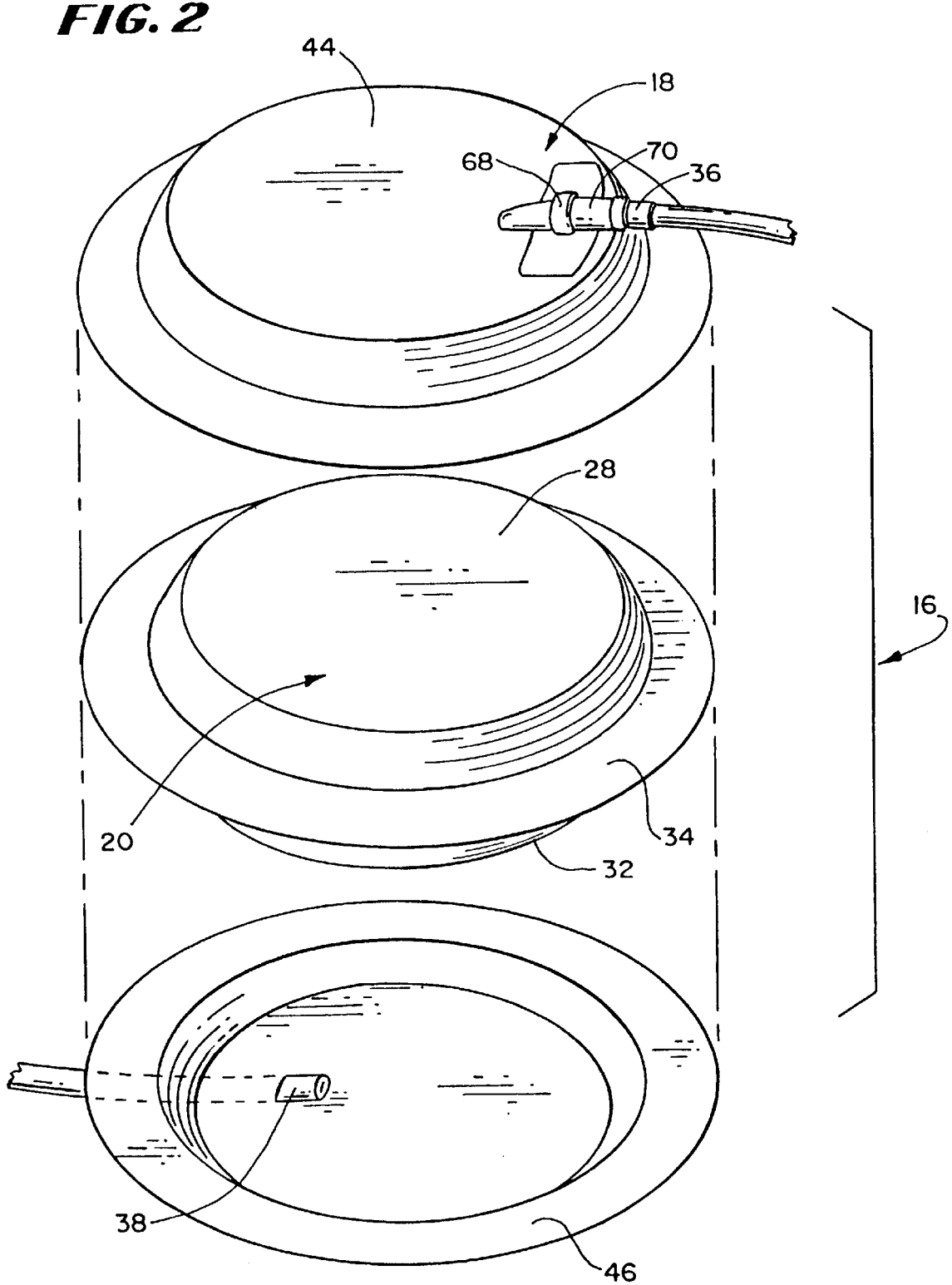
FIG. 2 is an exploded perspective view of the filter device that is associated with the assembly shown in FIG. 1, showing the filter pad assembly and surrounding housing.

The ports 36 and 38 are arranged about 180 degrees apart on opposite flow sides of the filter device 16 (see FIGS. 1 and 2). This orientation facilitates the set up and use of the filter device 18 in gravity flow conditions, as FIGS. 1 and 7 show.

The tangential, oppositely spaced ports 36 and 38 allow the direct attachment of transfer tubing 14 without kinking or bending. The tangential, oppositely spaced ports 36 and 38 also allow the filter device 16 to hang in a vertical position during use. This vertical position allows air trapped in the filter device 16 to vent through the filter pad assembly 20 during priming, preventing air entrapment and the need for auxiliary air vents.

Further details of the ports 36 and 38 will be described later.

The flexible housing 18 avoids the handling and processing problems rigid filter housings have presented in the past. Unlike a rigid housing, the flexible housing 18 will not puncture associated bags, which are also made of flexible plastic materials. Unlike a rigid housing, the flexible housing 18 conforms and is compliant to stress and pressures induced during use.

The flexible sheet 44 on the inlet side of the filter device 16 expands under the fluid head pressure of gravity flow. It thus creates a natural pressure manifold, which evenly distributes the fluid across the inlet face of the filter pad assembly 20. This assures that entrapped air is vented and that the fluid flows through the filter pad assembly 20 under uniform pressure and distribution.

When the distance between the filter device 16 and the source container is at a determinable amount (approximately 0.75 meter), the fluid head pressure within the inlet side is sufficient for the filter device 12 to become self-priming. The user is not required to "squeeze prime" the filter device 16, by squeezing the source container.

As the fluid container empties, negative pressure is created downstream of the filter device 16. Because the inlet and outlet sheets 44 and 46 of the housing 18 are flexible, they will collapse around the space occupied by the filter pad assembly 20. Fluid drains from the outlet side without the use of an auxiliary air vent.

Furthermore, the flexible housing 18 will not crack during heat sterilization. The flexible housing 18 also does not impede heat penetration during heat sterilization processes. Instead, the housing 18 accommodates uniform heat penetration into the filter pad assembly 20.

In the illustrated and preferred embodiment (as FIG. 3 best shows), the filter pad assembly 20 comprises a composite of three media regions 28/30/32.

The first media region 28 serves as a prefilter. Its purpose is to remove microaggregates of cellular blood components that can form in red blood cells after collection.

The second media region 30 serves as a leukocyte removal filter.

The third media region 32 serves as a manifold. It keeps the downstream side of the filter pad assembly 20 open to fluid flow, despite the presence of a negative fluid head pressure that pulls the downstream side of the flexible housing 18 (i.e., flexible sheet 46) in against the third media region 32.

Figure 5:
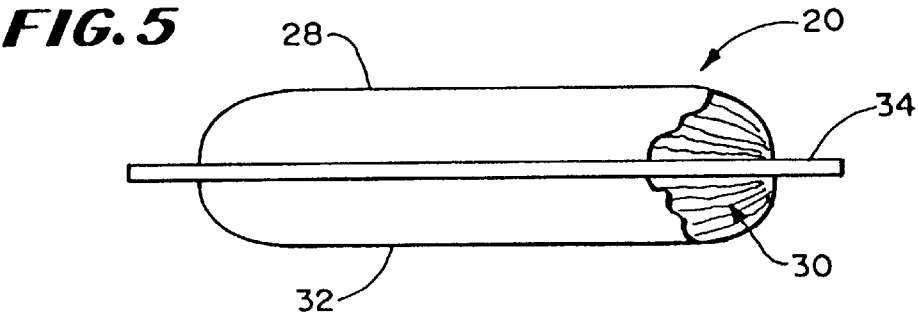
FIG. 5 is a side view of the composite filter pad assembly that is formed in FIG. 4.

As FIGS. 2 and 5 best show, a sealed region 34 joins the three media regions 28/30/32 at their peripheries. At least one of the media regions 28/30/32 extends above and below the sealed periphery 34. The region 34 is created by the application of heat and pressure, as will be described later.

In the illustrated and preferred embodiment (see FIG. 5), the pad assembly 20 is essentially symmetrical with respect to the sealed region 34; that is, the thickness of the filter pad assembly 20 that rises above the sealed reagion 34 is generally the same as the thickness of the filter pad assembly 20 that extends below the sealed region 34.

The sealed region 34 comprises a rigid, flat surface. It bonds the peripheries of the media regions 28/30/32 to each other. This prevents fluid being filtered from leaking past or bypassing one or more of the media regions 28/30/32.

As will be described in greater detail later, the rigid, flat surface the seal region 34 presents also presents a surface to which the flexible housing 18 can be bonded.

The First Media Region

While the constituents of the first media region 28 can vary, in the preferred embodiment, the first media region 28 comprises a needled assembly of three non-woven polyester fiber mats. The region 28 has an overall thickness of about 2 millimeters.

In the preferred embodiment, the fibers differ in denier among the three mat layers. The first mat layer comprises 1.0 denier polyester fiber (available from Hoescht Corporation, as L30 Fiber). The second mat layer comprises 1.5 denier polyester fiber (available Hoescht Corporation, as 224 Fiber). The third mat layer comprises 3.0 denier polyester fiber (also available as Hoescht 224 Fiber).

Components for the needled assembly can be purchased from Hoescht Corporation.

The Second Media Region

In the preferred embodiment (see FIG. 3), the second media region 30 comprises five individual layers 40 of a non-woven fiber media stacked one above the other.

In the preferred embodiment, each layer 40 of the second media region 30 has the same composition. Each layer 40 comprises web of interlocked polyester fibers, fiberglass fibers, and cellulose acetate fibrets made in accordance with the teaching of Heagle et al. U.S. Pat. No. 5,190,657, which is incorporated into this Specification by reference.

While the thickness of each individual layer 40 can vary, in the illustrated embodiment, each individual layer 40 has a nominal thickness of about 2 millimeters. The composite thickness of the 5 layer second media region 30 is therefore about 10 millimeters.

The precise composition and mix of the fiber components within each layer 40 can vary. In the preferred embodiment, the mix of interlocked fibers in each layer 40 constitutes about 75% by weight of 0.5 denier polyester fiber (made by Teijin Corporation, Type TK04N); about 10% by weight of microglass fiber (made by Schuller Corporation, Type Code 106); and about 5% by weight of cellulose acetate fibrets (made by Hoechst Corporation).

The interlocked fibers in each layer 40 are supported on a core sheath structure of polyolefin fibers that constitutes about 10 percent by weight of the layer (made by Chisso Corporation, Type EKC).

To reduce the incidence of particle shedding, each layer 40 is preferably coated after assembly by spraying with an acrylic emulsion. The acrylic emulsion coating serves to significantly reduce the incidence of particle shedding within the pad assembly 20.

It has been observed empirically the emulsion that is sprayed on the layer 40 should not constitute more than about 0.3% acrylic by volume. The use of an emulsion that is greater than 0.3% acrylic by volume has been observed to degrade the leukocyte depletion capabilities of the layer 40. It is believed that the degradation occurs because the thickness of the coating applied to the fibers begins to constrict the tortuous fluid paths through the layer 40.

An acrylic volume of 0.3% or less in the emulsion maximizes the intended anti-shedding effect without compromising the leukocyte depletion capabilities of the layer 40.

In the preferred embodiment, a 0.25% percent acrylic emulsion made by Rohm and Haas (Type HA8) is used. Each layer 40 so coated meets the AAMI particle shedding requirements for filtration devices.

It has also been determined that, to maximize the leukocyte removal efficiency of the second media region 30, a composite thickness for the second region 30 should exceed about 6 mm but should not exceed about 10 mm. Preferably, multiple layers should be used to obtain this composite nominal thicknesses.

A significant increase in leukocyte removal is observed when four individual layers of 2 mm nominal thickness each are used, as compared to three individual 2 mm layers. Still further increases are observed when a fifth 2 mm layer is added.

The further addition of individual layers beyond five (exceeding a total composite nominal thickness about 10 mm) does not incrementally increase leukocyte removal efficiencies. However, above about 10 mm, increasingly significant incremental decreases in flow rates through the pad are observed that offset the increased removal efficiencies.

It is believed that more than three, and optimally five, individual layers of 2 mm thickness strike an effective balance between considerations of flow rate and leukocyte removal efficiencies. The five layer pad assembly for the second media region meets AABB guidelines, which requires an output volume that is at least 90% of the input volume.

The five layer pad assembly also effectively removes leukocytes from red blood cells, providing as much as a 3 to 5 log reduction in the number of leukocytes.

The Third Media Region

The third media region 32 comprises a fluid manifold to promote uniform flow out of the filter pad assembly 20 through the outlet port 38.

In use, gravity flow through the filter device 16 creates positive fluid head pressure on the upstream side of the housing 18 (i.e, the sheet 44, which faces the first media region 28). This positive pressure causes the upstream sheet 44 of the flexible housing 18 to flex outward, like a balloon.

In use, a negative fluid head develops on the downstream side of the housing 18 (i.e., the sheet 46, which faces the third media layer 30) as the fluid source empties. This negative pressure causes the both the upstream and downstream sheets 44 and 46 to flex inward.

In the absence of the third media region 32, the inwardly flexed downstream sheet 46 would press directly against the downstream layer 40 of the pad assembly 20, sealing it close. In other words, in the absence of the third media region 32, the negative head pressure would occlude the downstream side of the flexible filter housing 18.

The third media region 32 interrupts the occluding surface contact between the downstream side of the housing and the second media region 30, keeping the flow path open in the face of negative head pressure.

The third media region 32 can comprise an embossed or textured surface on the inside surface of the outlet sheet 46 of the housing 18.

In the illustrated embodiment, the third media region 32 comprises a screen of woven mesh or knitted fiber. The region 32 preferably comprises a knitted layer of polyester fibers, like a 70 denier polyester knit made by DuPont (Type 34).

Figure 3:
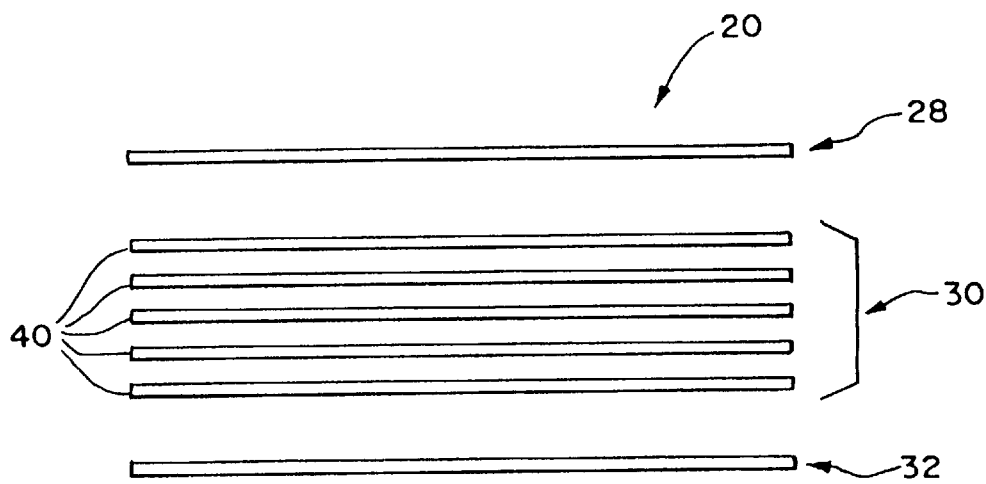
FIG. 3 is an exploded side section view of the first, second, and third media regions of the filter pad assembly shown in FIG. 2.
Figure 4:
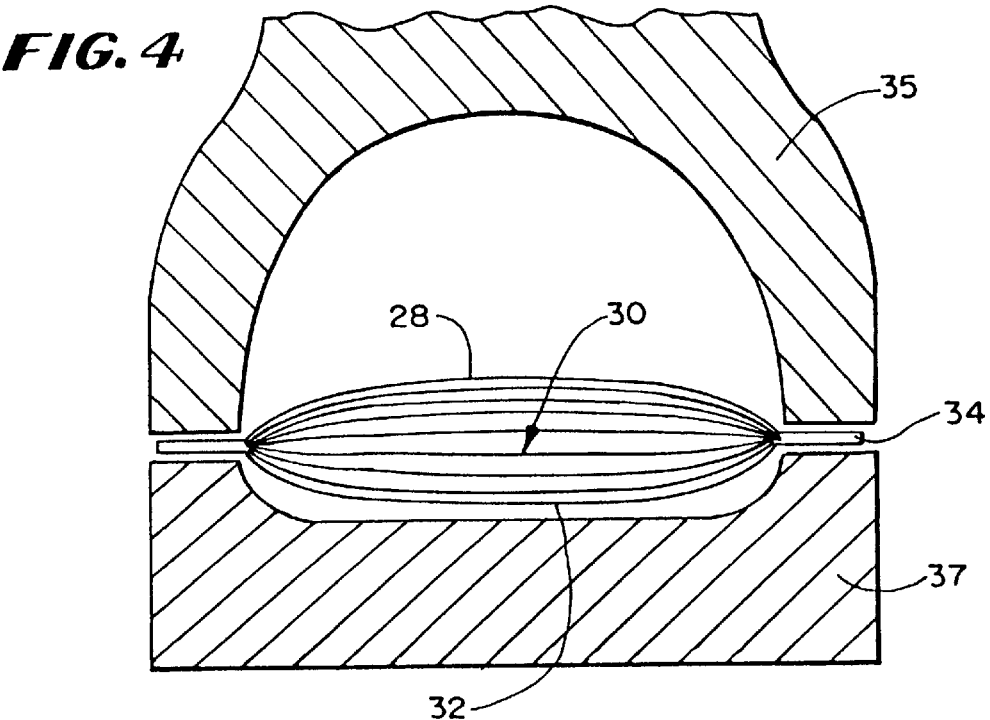
FIG. 4 is a side section view of the formation of the peripheral seal about the first, second, and third media regions to create the filter pad assembly using an ultrasonic sealing tool.

As FIG. 3 shows, the first, second and third media regions 28/30/32 are stacked one above the other. As FIG. 4 shows, the regions 28/30/32 are fused together about their peripheries by pressure and heat to form the seal 34 and the essentially symmetric pad assembly 20 shown in FIG. 5.

In the illustrated embodiment, the pad assembly 20 measures about 3.4 inches in overall diameter (about the peripheral seal 34) and about 0.5 inch in overall height. The peripheral seal 34 itself measures about 0.044 inch in thickness and about 0.226 inch in width.

Various techniques can be used to peripherally fuse the regions 28/30/32 together. In the preferred embodiment (as FIG. 4 shows), the regions are welded together ultrasonically. The operating ranges for making the sonic weld can vary according to the materials used.

One representative embodiment uses an ultrasonic welder comprising a horn 35 and an anvil 37. The horn 35 is operated at 20 Khz, tuned in a range from 100 to 300 watts. The horn 35 is operated at a temperature of about 85 degrees Fahrenheit, with a weld time of about 1.8 seconds; a hold time of about 3.0 seconds; a weld delay of about 1.0 seconds; an afterburst of about 0.10 second; and a pressure of about 105 PSI.

The essential symmetry of the filter pad assembly 20 maximizes the surface area available for leukocyte removal, as the peripheral seal 34 occupies only a relatively small area of the overall pad assembly 20.

The essential symmetry of the pad assembly 20 also simplifies the final assembly of the pad assembly 20 within the housing 18 of the filter device 16, as will be demonstrated shortly.

The Filter Housing

As FIG. 6 show, the filter device housing 18 comprises two sheets 44 and 46 of flexible, inert, thermoplastic material. For example, plasticized medical grade polyvinyl chloride material can be used.

The sheets 44 and 46 are fused about their periphery by the application of heat and pressure against opposite sides of the peripheral seal 34 of the filter pad assembly 20.

The sheet 44 overlies the first media region 28 of the filter pad assembly 20. The sheet 46 overlies the third media region 32 of the filter pad assembly 20.

As FIG. 6A best shows, the fused perimeters of the sheets 44 and 46 form an integrated or composite seal 48. The inner portion 49 of the seal 48 integrally bonds the material of the sheets 44/46 with the peripheral seal 34 of the filter pad assembly 20. The outer portion 51 of the seal 48 bonds the material of the sheets 44/46 together.

The exterior of the sheets 44 and 46 conform about the symmetrical shape of the enclosed filter pad assembly 20.

The integrated seal 48 encapsulates the filter pad assembly 20 between the housing sheets 44/46 in a straightforward, one step process.

The integrated seal 48 can be accomplished in various ways. In the illustrated embodiment (see FIG. 6), a radiofrequency (RF) welder comprising upper and lower dies 53 and 55 (see FIG. 6) is used.

The operating ranges for making the seal 48 can vary according to the materials used. For example, one representative process uses a 12 kilowatt RF generator and applies pressures between the two dies 53 and 55 in excess of 1000 pounds to create the seal 48. Since the peripheral seal 34 of the pad assembly 20 is not itself RF sealable, high pressure must be used to integrally bond the plastic sheets 46/48 to the seal 34 in the inner portion 49 of the seal 48, as FIG. 6A shows.

As before described, the filter device 16 includes the inlet port 36 and the outlet port 38. The ports 36 and 38 are joined to the transfer tubing 14 to conduct red blood cells into and out of the filter device 16.

In the illustrated and preferred embodiment, the ports 36 and 38 are spaced away from the integrated seal 48. The ports 36 and 38 also extend tangentially with respect to the filter pad assembly 20. The inlet port 36 is associated with the sheet 44, while the outlet port 38 is associated with the sheet 48.

The ports 36 and 38 are preformed in their respective sheet 44/46 before making the integrated seal 48. The technique of forming each port 36/38 in the sheets 44/46 is described in copending related U.S. patent application Ser. No. 08\121,344, filed Sep. 14, 1993, and entitled "Medical Container Port.

As both ports 36/38 are formed in the same way, only the formation of the inlet port 36 will be described in detail.

As seen in FIG. 9, a slit 50 is formed in sheet 44 at a location spaced from the periphery of sheet 44. This slit 50 is made in the sheet 44 before it is integrally welded to the filter pad assembly 20.

The slit 50 is made of a length to just accept the outer diameter of a tube 52 of thermoplastic material (see FIG. 10).

As seen in FIGS. 12 to 14, a pair of opposed dies 54 and 56 are positioned on opposite sides of slit 50 and tube 52. A mandrel 58 having an outer diameter equal to the inner diameter of tube 52 is inserted within tube 52, as seen in FIGS. 12 and 13. The dies 54 and 56 are provided with aligned concave recesses 60 and 62 that together form a circular bore. Central grooves 64 and 66 are formed in recesses 60 and 62, respectively.

The sheet 44, dies 54 and 56, tube 52, and mandrel 58 are all brought together into the position shown in FIG. 13. Preferably, a stop is provided to accurately space the dies 54 and 56 apart from each other.

Radiofrequency (RF) energy is then applied through dies 54 and 56 and mandrel 58 to soften the thermoplastic material of tube 52 and sheet 44. The dies 54 and 56, which remain relatively cool, act as a mold for the softened material.

Material from tube 52 flows as indicated into grooves 64 and 66 to form an enlargement of material or ridge 68. The ridge 68 reinforces the junction between tube 52 and slit 50 in the sheet 44.

A depression 70 of slightly decreased thickness is also formed in the sheet 44 surrounding the completed port 36. The resultant port 36 is, thus, reinforced at its potentially weakest point and is capable of withstanding substantial pressure.

After a brief period of cooling, the thermoplastic material hardens sufficiently and dies 54 and 56 and mandrel 58 can be withdrawn.

Placement of the ports 36 and 38 on the sheets 44 and 46 away from the integrated seal 48 eliminates the need to bring the ports 36 and 38 through the integrated seal 48. The port placement further complements the straightforward, single step sealing process for integrating the housing 18 and the filter pad assembly 20.

In a preferred embodiment the invention, each sheet 44 and 46 is formed of polyvinylchloride having a thickness of about 0.015 inch. A port tube 52 having a wall thickness of about 0.02 inch, an outside of about 0.228 inch and a length of about 0.75 inch is used. The mandrel 58 is preferably about 0.003 inch smaller than the inner diameter of the tube 52, and the mandrel 58 extends approximately ³⁄₁₀ of one inch beyond the end of the tube 52.

RF energy is applied for the dielectric heating step through a switching mechanism which first feeds the energy to the mandrel 58 and then to the opposing dies 54 and 56. Preferably, a mechanical stop is used to ensure that the two dies are separated by about 0.012 inch. Since the dies are not greatly heated by the dielectric heating, they can be withdrawn after a brief cooling period.

In accordance with the invention, a tube 52 is generally preferred that has a wall thickness of approximately 20–70% thicker than the sheet 44/46. This ensures that an adequate amount of thermoplastic material is available to form rib 40 in the finished port opening joint. It is also preferred that slit 50 be no longer than the diameter of the tube 52 thereby ensuring a tight initial fit between the sheet 44 and tube 52.

The sheet 44/46 surrounding the port 36/38 is preferably at least 80% of the original thickness of the sheet 44/46. The wall of tube 52 is thinned to approximately 60–70% of its original thickness.

The integrated housing 18 and filter pad assembly 20 permits the manufacture of a strong, fluid tight, yet flexible filter device 16.

Characterizing the Leukocyte Depletion Media

Fibrous leukocyte depletion filter media have in the past been characterized in terms of their average fiber diameter. For example, Watanabe et al. U.S. Pat. No. 4,701,267 describes and claims a leukocyte filter of a non-woven fabric where the fibers of the fabric have an average diameter of from 0.3 microns to less than 3 microns.

However, it is not possible to physically measure and quantify the average fiber diameter of a complex, multiple fiber matrix like that found in second media region 30, where leukocyte depletion occurs. This is true, not only because of the intricacy of the physical structure of the matrix, but also because of the geometry of the fibrets that form part of the matrix.

Keith et al. U.S. Pat. No. 4,274,914 further describes the nature of the fibrets, which have also been called "fibrillated particles." They typically have overall lengths of less than about 1000 microns and overall widths of about 0.1 to 50 microns. They comprise fibers from which branches of fine mini-fibers (called fibrils) radiate. The fibrils are extremely small, e.g., less than 0.01 microns in diameter. It is not possible to physically measure and then average the diameter of the multitude of fibrils present in each layer 40.

Still, average fiber diameter remains one characteristic useful for correlating physical structure with desired performance criteria.

One aspect of the invention provides a methodology to quantify the average fiber diameter in complex multiple fiber matrixes, even when the diameter of one or more of the fibers cannot be physically ascertained.

The derivation procedure that embodies the features of this aspect of the invention comprises four steps.

STEP (1) determines the density and diameter of those component fibers which can be physically measured by conventional methods. In the described implementation, density is expressed in g/cm³, and diameter is expressed in cm (or microns). Still, other units of measurement can be used, as long as they are consistently applied through the derivation procedure.

STEP (2) derives the diameter of each component fiber for which diameter cannot be physically measured by conventional methods. The derivation relies upon the Area-to-Weight ratio (A/W) for the fiber and the density of the polymer of the fiber. A/W is expressed in cm²/g and density is expressed in g/cm³. STEP (2) then derives the diameter of the fibers using the following equation:

$$d = \frac{4}{\rho} \times \frac{1}{A/W}$$

where:
   d is the diameter of the fiber (in cm, or, by multiplying cm by 10,000, in microns);
   $\rho$ is the density of the fiber (in g/cm³); and
   A/W is the area-to-weight ratio of the fiber (in cm²/g).

STEP (3) derives the length (in cm) of each fiber material present in 1 gram of the matrix, using the following equation:

$$L_i = \frac{4Q_i}{\pi \rho_i d_i^2}$$

where:
   $i$ is the selected fiber;
   $L_i$ is the length of the selected fiber (in cm) present in one gram of the matrix;
   $Q_i$ is the weight fraction of the selected fiber (in g) (expressed as a decimal; e.g., 10%=0.1 g);
   $\pi$ is 3.1417;
   $d_i$ is the diameter of the selected fiber (in cm); and
   $\rho_i$ is the density of the selected fiber (in g/cm³).

The length $L_i$ can be expressed in simplified terms as a ratio based upon the shortest absolute fiber length present in the matrix. This simplifying conversion avoids working with large numbers (a consideration particularly when the calculation is done manually) and is made by dividing each fiber length by the length of the shortest fiber present. The converted quantity is dimensionless and is expressed terms of a number length per unit length of the shortest fiber present in the matrix. Alternatively, the length $L_i$ can be retained in its unsimplified form (expressed in cm per cm of the shortest fiber present) during the calculation procedure.

STEP (4) derives the number average diameter of all fibers present in the matrix by adding together the product of the length $L_i$ (expressed in cm) and diameter (in cm) an divided by the length $L_i$ (in cm), for each fiber, using the following equation:

$$\frac{\Sigma L_i \times d_i}{\Sigma L_i}$$

where:
   i is the fiber;
   $L_i$ is the length of the fiber (in cm);
   $d_i$ is the diameter of the fiber (in cm).

The following Example 1 applies the above-described methodology to derive the average diameter of the fibers present in an individual layer 40 of the second media region 30.

EXAMPLE 1

Each individual layer 40 comprises the following fibers:
Polyester and Core Sheath—85% by weight.
Fiberglass—10% by weight.
Cellulose Acetate Fibrets—5% by weight.

STEP (1): The density and diameter of the polyester and fiberglass fibers can be ascertained by conventional methods, as follows:
   Fiberglass
      Density=2.5 g/cm³; and
      Diameter=0.000065 cm (0.65 micron)
   Polyester (including the core sheath)
      Density=1.38 g/cm³; and
      Diameter=0.001 cm (10 microns).

STEP (2): The diameter of the cellulose acetate fibrets fibers cannot be measured by conventional methods. The diameter is thereby determined based upon the area-to weight ratio of cellulose acetate fibrets and the density of cellulose acetate (each of which can be conventionally determined), as follows:
   Area-to-weight ratio of cellulose acetate (for fibret fiber material): 200,000 cm²/g: and
   Density of cellulose acetate (for fibret fiber material): 1.28 g/cm³
   The calculated diameter of the fibrets is 0.00001563 cm (0.1563 micron).

STEP (3): The lengths of polyester; fiberglass; and fibrets in 1 g of the layer 40 is determined, as follows:
   The shortest fiber length is polyester, which is calculated to be 784,639.5 cm per gram of the layer 40; and, if divided by its length for simplification purposes, $L_{polyester}$ is 1 cm;
   The fiber length of fiberglass is calculated to be 12,060,463 cm per gram of the layer 40; and, if divided by the length of polyester (784,639.5) for simplification purposes, $L_{Fiberglass}$ is 15.371 cm per cm of polyester fiber; and
   The fiber length of fibrets is calculated to be 204,000,000 cm per gram of the layer 40; and, if divided by the length of polyester (784,639.5) for simplification purposes, $L_{Fibret}$ is 260.598 cm per cm of polyester fiber.

STEP (4): By adding together the product of the length $L_i$ (expressed in cm/cm of polyester) and diameter $d_i$, divided by the length $L_i$ (expressed in cm/cm of polyester) for each fiber (when "i" constitutes polyester; then fiberglass; and then fibrets), the number average fiber diameter of the fibers present is each layer 40 is derived to be 0.0000219 cm (0.219 micron).

The change in the number average fiber diameter for a given layer 40 in response to changes in the relative weight percentages of the individual fibers can be calculated and placed in a look-up table format using a conventional computer spreadsheet program.

FIG. 15 shows a representative look-up table, calculated according to the above identified methodology, of the number average fiber diameters for a media layer comprising polyester fiber/core sheath (d=10 microns and $\rho$=1.38 g/cm³); fiberglass (d=0.65 micron and $\rho$=2.5 g/cm³); and cellulose acetate fibrets (A/W=200,000 cm²/g and $\rho$=1.28 g/cm³). FIG. 15 shows the change in average number fiber diameter occasioned by changing the weight percentages of fiberglass (y-axis) and/or fibrets (x-axis), with the polyester/core sheath comprising the remaining percentage.

As the following Example 2 shows, the number average fiber diameter defines a useful characteristic for correlating physical structure with performance in complex, multiple fiber leukocyte depletion media. The number average fiber diameter can serve as a predictor of expected performance during the development of such complex media. It can also serve as a practical quality control parameter for monitoring the manufacture of such complex media.

EXAMPLE 2

Table 1 list the results of empirical tests that measured changes in leukocyte depletion (in whole blood), in mean flow pore size, and in whole blood flow time in complex leukodepletion media comprising polyester, fiberglass, and fibret fibers, when assembled in pads of different thicknesses and different number average fiber diameters.

TABLE 1

SAMPLE 1

Weight Percent

| | |
|---|---|
| Fiberglass | 10% |
| CA Fibrets | 5% |
| Polyester | 75% |
| Core Binder | 10% |

No. Average

| | | |
|---|---|---|
| Fiber Diameter | | .219 microns |
| Thickness (mm) | 2.1 | 2.1 |
| Max. Pore Size | | 17.110 Microns |
| Min. Pore Size | | 2.529 Microns |
| Mean Flow Pore Size | | 5.028 Microns |

As Measured by Coulter ™ Porometer II
Whole Blood Flow

| | | |
|---|---|---|
| Time/35 ml | 86 min | 127 min |
| Log Depletion | 0.43 | 0.25 |

SAMPLE 2

Weight Percent

| | |
|---|---|
| Fiberglass | 7% |
| CA Fibrets | 3% |
| Polyester | 83% |
| Core Binder | 7% |

No. Average

| | | |
|---|---|---|
| Fiber Diameter | | .250 Micron |
| Thickness (mm) | 1.9 | 2.1 |
| Max. Pore Size | | 50 Microns |
| Min. Pore Size | | 4.067 Microns |
| Mean Flow Pore Size | | 8.295 Microns |

As measured by Coulter ™ Porometer II
Blood Flow

| | | |
|---|---|---|
| Time/35 ml | 39 min | 46 min |
| Log Depletion | 0.31 | 0.19 |

SAMPLE 3

Weight Percent

| | |
|---|---|
| Fiberglass | 7% |
| CA Fibrets | 3% |
| Polyester | 83% |
| Core Binder | 7% |

No. Average

| | | | |
|---|---|---|---|
| Fiber Diameter | | | .250 Micron |
| Thickness (mm) | 2.2 | 2.4 | 2.1 |
| Max. Pore Size | | | 50 Microns |
| Min. Pore Size | | | 3.875 Microns |
| Mean Flow Pore Size | | | 8.68 Microns |

As measured by Coulter ™ Porometer II
Blood Flow

| | | | |
|---|---|---|---|
| Time/35 ml | 42 min | 66 min | 38 min |
| Log Depletion | 0.27 | 0.06 | 0.49 |

TABLE 1-continued

SAMPLE 4

Weight Percent

| | |
|---|---|
| Fiberglass | 7% |
| CA Fibrets | 7% |
| Polyester | 73% |
| Core Binder | 13% |

No. Average

| | | |
|---|---|---|
| Fiber Diameter | | .197 Micron |
| Thickness (mm) | 2.5 | 2.2 |
| Max. Pore Size | | 50 Micron |
| Min. Pore Size | | 2.721 Micron |
| Mean Flow Pore Size | | 5.412 Micron |

As measured by Coulter ™ Porometer II
Blood Flow

| | | |
|---|---|---|
| Time/35 ml | 79 min | 67 min |
| Log Depletion | 0.41 | 0.42 |

SAMPLE 5

Weight Percent

| | |
|---|---|
| Fiberglass | 13% |
| CA Fibrets | 7% |
| Polyester | 73% |
| Core Binder | 7% |

No. Average

| | | | |
|---|---|---|---|
| Fiber Diameter | | | .206 Micron |
| Thickness (mm) | 2.05 | 2.3 | 2.3 |
| Max. Pore Size | | | 13.72 Micron |
| Min. Pore Size | | | 2.145 Micron |
| Mean Flow Pore Size | | | 3.682 Micron |

As measured by Coulter ™ Porometer II
Blood Flow

| | | | |
|---|---|---|---|
| Time/35 ml | 329 min | 405 min | 204 min |
| Log Depletion | 1.07 | 0.06 | 0.94 |

SAMPLE 6

Weight Percent

| | |
|---|---|
| Fiberglass | 13% |
| CA Fibrets | 3% |
| Polyester | 71% |
| Core Binder | 13% |

No. Average

| | | | |
|---|---|---|---|
| Fiber Diameter | | | .267 Micron |
| Thickness (mm) | 2.15 | 2.35 | 2.1 |
| Max. Pore Size | | | 15.81 Microns |
| Min. Pore Size | | | 2.721 Microns |
| Mean Flow Pore Size | | | 4.836 Microns |

As measured by Coulter ™ Porometer II
Blood Flow

| | | | |
|---|---|---|---|
| Time/35 ml | 159 min | 327 min | 132 min |
| Log Depletion | 1.11 | 0.07 | 0.93 |

SAMPLE 7

Weight Percent

| | |
|---|---|
| Fiberglass | 7% |
| CA Fibrets | 5% |
| Polyester | 81% |
| Core Binder | 7% |

No. Average

| | | | |
|---|---|---|---|
| Fiber Diameter | | | .213 Micron |
| Thickness (mm) | 2.5 | 2.1 | 2.3 |
| Max. Pore Size | | | 25.49 Microns |
| Min. Pore Size | | | 3.49 Microns |
| Mean Flow Pore Size | | | 6.565 Microns |

TABLE 1-continued

As measured by Coulter ™ Porometer II
Blood Flow

| | | | |
|---|---|---|---|
| Time/35 ml | 75 min | 123 min | 60 min |
| Log Depletion | 0.5 | 0 | 0.59 |

SAMPLE 8

Weight
Percent

| | |
|---|---|
| Fiberglass | 7% |
| CA Fibrets | 7% |
| Polyester | 76% |
| Core Binder | 10% |

No. Average

| | | |
|---|---|---|
| Fiber Diameter | .197 Micron | |
| Thickness (mm) | 2.1 | 2.2 |
| Max. Pore Size | 50 Microns | |
| Min. Pore Size | 2.529 Microns | |
| Mean Flow Pore Size | 5.219 Microns | |

As measured by Coulter ™ Porometer II
Blood Flow

| | | |
|---|---|---|
| Time/35 ml | 98 min | 136 min |
| Log Depletion | 0.35 | 0.24 |

SAMPLE 9

Weight
Percent

| | |
|---|---|
| Fiberglass | 10% |
| CA Fibrets | 7% |
| Polyester | 76% |
| Core Binder | 2% |

No. Average

| | | |
|---|---|---|
| Fiber Diameter | .202 Micron | |
| Thickness (mm) | 2 | 2.3 |
| Max. Pore Size | 18.64 Micron | |
| Min. Pore Size | 2.145 Micron | |
| Mean Flow Pore Size | 4.067 Micron | |

As measured by Coulter ™ Porometer II
Blood Flow

| | | |
|---|---|---|
| Time/35 ml | 250 min | 146 min |
| Log Depletion | 0.46 | 0.86 |

EXAMPLE 10

Weight
Percent

| | |
|---|---|
| Fiberglass | 7% |
| CA Fibrets | 3% |
| Polyester | 77% |
| Core Binder | 13% |

No. Average

| | | |
|---|---|---|
| Fiber Diameter | .250 Micron | |
| Thickness (mm) | 2.3 | 2.3 |
| Max. Pore Size | 50 Microns | |
| Min. Pore Size | 4.067 Microns | |
| Mean Flow Pore Size | 7.526 Microns | |

As measured by Coulter ™ Porometer II
Blood Flow

| | | |
|---|---|---|
| Time/35 ml | 37 min | 35 min |
| Log Depletion | 0.21 | 0.36 |

SAMPLE 11

Weight
Percent

| | |
|---|---|
| Fiberglass | 13% |
| CA Fibrets | 3% |
| Polyester | 77% |
| Core Binder | 7% |

No. Average

| | | |
|---|---|---|
| Fiber Diameter | .267 Micron | |
| Thickness (mm) | 2.2 | 2.4 |
| Max. Pore Size | 20.48 Microns | |
| Min. Pore Size | 2.914 Microns | |
| Mean Flow Pore Size | 5.412 Microns | |

As measured by Coulter ™ Porometer II
Blood Flow

| | | |
|---|---|---|
| Time/35 ml | 124 min | 133 min |
| Log Depletion | 0.9 | 1 |

SAMPLE 12

Weight
Percent

| | |
|---|---|
| Fiberglass | 13% |
| CA Fibrets | 5% |
| Polyester | 72% |
| Core Binder | 10% |

No. Average

| | | |
|---|---|---|
| Fiber Diameter | .225 Micron | |
| Thickness (mm) | 2.3 | 2.3 |
| Max. Pore Size | 18.64 Microns | |
| Min. Pore Size | 2.336 Microns | |
| Mean Flow Pore Size | 4.643 Microns | |

As measured by Coulter ™ Porometer II
Blood Flow

| | | |
|---|---|---|
| Time/35 ml | 151 | 121 |
| Log Depletion | 0.49 | 0.56 |

SAMPLE 13

Weight
Percent

| | |
|---|---|
| Fiberglass | 10% |
| CA Fibrets | 3% |
| Polyester | 77% |
| Core Binder | 10% |

No. Average

| | | |
|---|---|---|
| Fiber Diameter | .259 Micron | |
| Thickness (mm) | 2.25 | 2 |
| Max. Pore Size | 33.77 Microns | |
| Min. Pore Size | 3.49 Microns | |
| Mean Flow Pore Size | 6.565 Microns | |

As measured by Coulter ™ Porometer II
Blood Flow

| | | |
|---|---|---|
| Time/35 ml | 101 min | 59 min |
| Log Depletion | 0.3 | 0.46 |

SAMPLE 14

Weight
Percent

| | |
|---|---|
| Fiberglass | 10% |
| CA Fibrets | 5% |
| Polyester | 72% |
| Core Binder | 13% |

No. Average

| | | | |
|---|---|---|---|
| Fiber Diameter | .219 Micron | | |
| Thickness (mm) | 2.2 | 2.45 | 2.05 |
| Max. Pore Size | 50 Microns | | |
| Min. Pore Size | 2.721 Microns | | |
| Mean Flow Pore Size | 5.412 Microns | | |

As measured by Coulter ™ Porometer II
Blood Flow

| | | | |
|---|---|---|---|
| Time/35 ml | 185 min | 109 min | 92 min |
| Log Depletion | −0.07 | 0.65 | 0.57 |

TABLE 1-continued

SAMPLE 15

| Weight Percent | | |
|---|---|---|
| Fiberglass | 7% | |
| CA Fibrets | 7% | |
| Polyester | 79% | |
| Core Binder | 7% | |
| No. Average | | |
| Fiber Diameter | .197 Micron | |
| Thickness (mm) | 2 | 2 |
| Max. Pore Size | 50 Microns | |
| Min. Pore Size | 3.106 Microns | |
| Mean Flow Pore Size | 5.989 Microns | |
| As measured Coulter ™ Porometer II | | |
| Blood Flow | | |
| Time/35 ml | 76 min | 57 min |
| Log Depletion | 0.25 | 0.36 |

SAMPLE 16

| Weight Percent | | |
|---|---|---|
| Fiberglass | 13% | |
| CA Fibrets | 7% | |
| Polyester | 67% | |
| Core Binder | 13% | |
| No. Average | | |
| Fiber Diameter | .206 Micron | |
| Thickness (mm) | 2 | 2.5 |
| Max. Pore Size | 14.69 Microns | |
| Min. Pore Size | 2.145 Microns | |
| Mean Flow Pore Size | 3.875 Microns | |
| As measured by Coulter ™ Porometer II | | |
| Blood Flow | | |
| Time/35 ml | 270 min | 208 min |
| Log Depletion | 0.47 | 0.97 |

SAMPLE 17

| Weight Percent | | |
|---|---|---|
| Fiberglass | 7% | |
| CA Fibrets | 5% | |
| Polyester | 81% | |
| Core Binder | 7% | |
| No. Average | | |
| Fiber Diameter | .213 Micron | |
| Thickness (mm) | 2.3 | 2.4 |
| Max. Pore Size | 33.77 Microns | |
| Min. Pore Size | 3.297 Microns | |
| Mean Flow Pore Size | 5.989 Microns | |
| As measured by Coulter ™ Porometer II | | |
| Blood Flow | | |
| Time/35 ml | 72 min | 81 min |
| Log Depletion | 0.43 | 0.17 |

Figure 16:
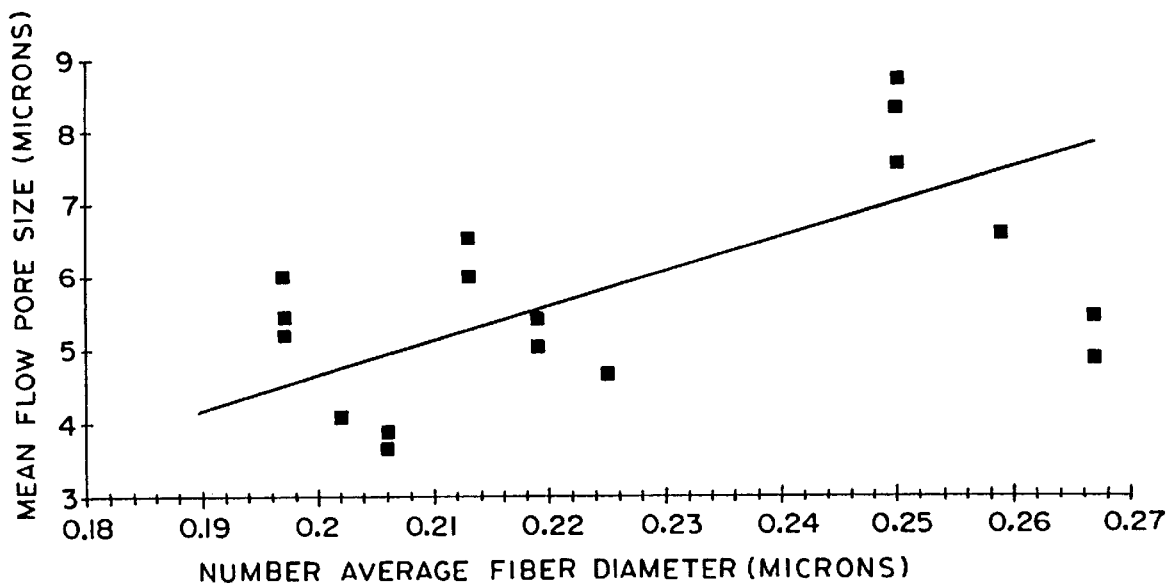
FIG. 16 charts the number average fiber diameter of the complex media (x-axis) against mean flow pore size (y-axis) of the media based upon empirical data, showing a trend that correlates these two structural characteristics.

FIG. 16 charts the number average fiber diameter of the layers (x-axis) against mean flow pore size (y-axis), based upon the results listed in Table 1. FIG. 16 shows a trend that correlates these two structural characteristics.

Figure 17:
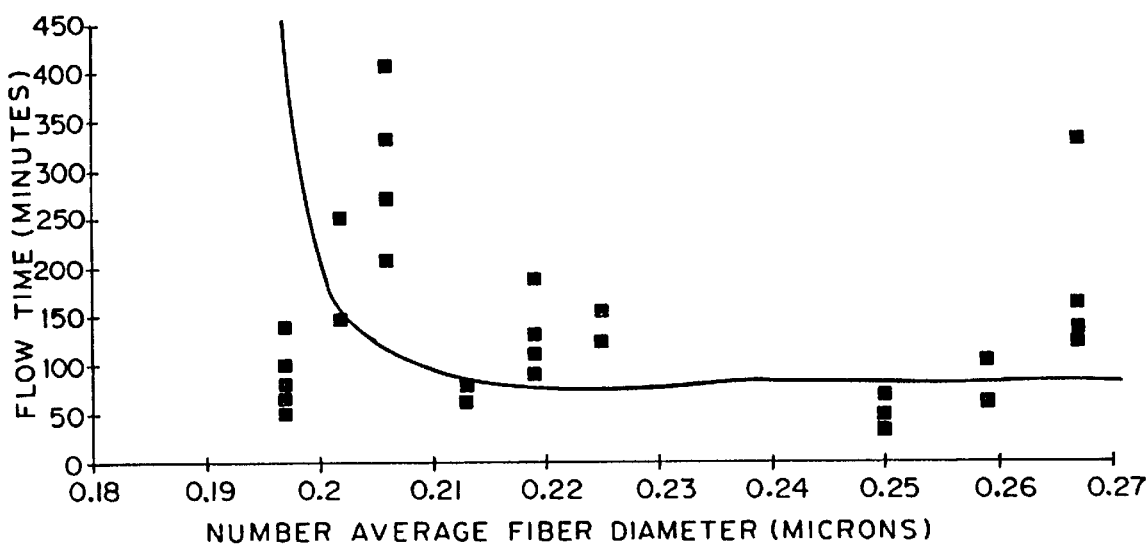
FIG. 17 charts the number average fiber diameter of the media (x-axis) against the flow time of whole blood (y-axis) through the media, based upon empirical data, showing a trend that correlates the structural characteristic (fiber diameter) with an expected performance characteristic (flow time)

FIG. 17 charts the number average fiber diameter of the layers (x-axis) against the flow time of whole blood (y-axis), based upon the results listed in Table 1. FIG. 17 also shows a trend that correlates the structural characteristic (fiber diameter) with an expected performance characteristic (flow time).

Figure 18:
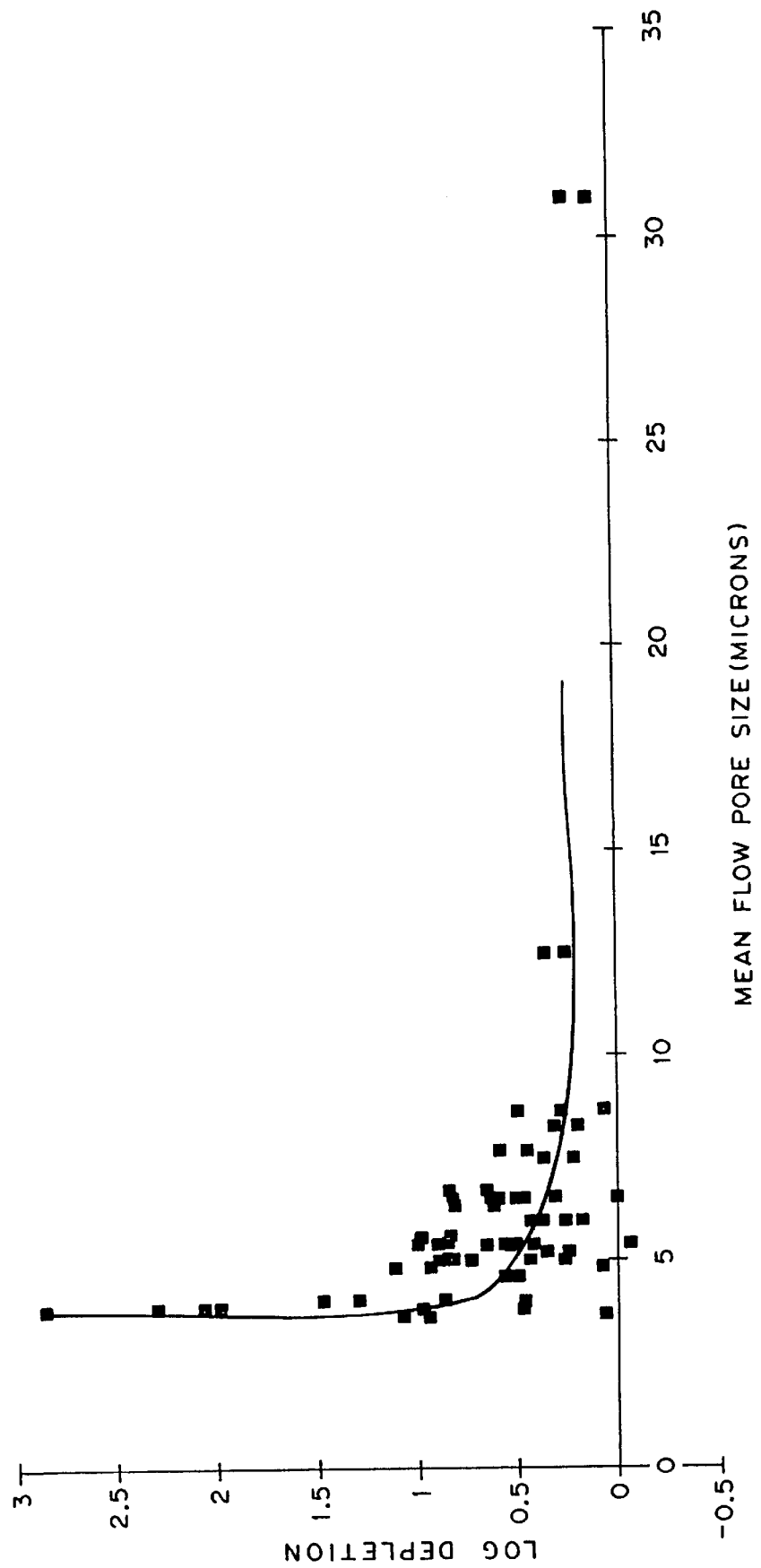
FIG. 18 charts the mean flow pore size (x-axis) of the media against the log depletion of leukocytes in whole blood (y-axis) passed through the media, based upon empirical data, showing a trend that correlates the physical characteristic (mean flow pore size) with an expected performance characteristic (leukocyte depletion).

FIG. 18 charts the mean flow pore size (x-axis) against the log depletion of leukocytes in whole blood (y-axis), based upon the results listed in Table 1. FIG. 18 further shows a trend that correlates the physical characteristic (mean flow pore size) with an expected performance characteristic (leukocyte depletion).

Based upon FIGS. 16 to 18, one has a reasonable basis to select a number average fiber diameter of no more than about 0.23 micron as a characteristic for the complex media layer. This number average fiber diameter correlates with an acceptable log reduction of leukocytes in whole blood at an acceptable whole blood flow rate.

More particularly, the 0.23 micron number average fiber diameter correlates with a mean flow pore size of about 5 to 6 microns, as the curve in FIG. 16 shows. A mean flow pore size of 5 to 6 microns, in turn, correlates with region of increasing leukocyte depletion on the curve shown in FIG. 18. The 0.23 micron number average also correlates with a region of stable, acceptable blood flow time on the curve shown in FIG. 17.

By specifying a number average fiber diameter larger than 0.23 micron, one increases the mean flow pore size of the media, as the curve is FIG. 16 indicates. This, in turn, shifts expected leukocyte depletion away from the more favorable region on the leukocyte reduction curve (as FIG. 18 shows), with no expected corresponding favorable shift in blood flow time (as FIG. 17 shows).

The follow claims set forth the features of the invention.

We claim:

1. A method for correlating average fiber diameter with performance for a filtration media comprising a matrix of a first component fiber having a first diameter and a second component fiber having a second diameter less than the first diameter, the method comprising the steps of (1) manufacturing the filter media with a selected matrix of the first component fiber and the second component fiber, (2) physically measuring the density and diameter of the first component fiber;

(3) deriving the diameter of the second component fiber without physical measurement using the following equation:

$$d = \frac{4}{\rho} \times \frac{1}{A/W}$$

where:

d is the diameter of the second component fiber (in cm, or, by multiplying cm by 10,000 in microns);

$\rho$ is the density of the second component fiber (in g/cm$^3$); and

A/W is the area-to-weight ratio of the second component fiber (in cm$^2$/g);

(4) deriving the length (in cm) of each first and second component fiber present in 1 gram of the matrix, using the following equation:

$$L_i = \frac{4Q_i}{\pi \rho_i d_i^2}$$

where:

$i$ is the selected fiber whose length is being derived;

$L_i$ is the length of the selected fiber (in cm) present in 1 gram of the matrix;

$Q_i$ is the weight fraction of the selected fiber (in g) (expressed as a decimal; e.g., 10%=0.1 g);

π is 3.1417;

$d_i$ is the diameter of the selected fiber (in cm); and $\rho_i$ is the density of the selected fiber (in g/cm³);

(5) deriving the number average diameter (in cm) of all first and second component fibers present in the matrix by adding together, for each first and second component fiber, the product of the length $L_i$ (in cm) and diameter (in cm) divided by the length $L_i$ (in cm), using the following equation:

$$\frac{\Sigma L_i \times d_i}{\Sigma L_i}$$

(6) observing a selected performance characteristic of the filtration matrix, (7) repeating steps (1) to (6) with different matrixes of the first and second component fibers, each matrix selected to create a different number average diameter of first and second component fibers, and (8) expressing change in the selected performance characteristic as a function of change in number average diameter of the first and second component fibers present in the filtration media matrixes.

2. A method according to claim 1 wherein, in step (4), length $L_i$ is expressed as a ratio based upon the shortest absolute fiber length present in the matrix by dividing each fiber length by the length of the shortest fiber present, $L_i$ being thereafter expressed in terms of cm per cm of the shortest fiber present.

3. A method for correlating average fiber diameter with performance for a filtration media comprising a matrix of polyester fibers, fiberglass fibers, and cellulose acetate fibrets comprising the steps:

(1) manufacturing the filter media with a selected matrix of the polyester fibers, fiberglass fibers, and cellulose acetate fibers, (2) deriving the length of each fiber present in 1 gram of the matrix, using the following equation:

$$L_i = \frac{4Q_i}{\pi \rho_i d_i^2}$$

where:

$i$ is the selected fiber (polyester, fiberglass, and cellulose acetate fibrets);

$L_i$ is the length of the selected fiber (in cm) present in 1 gram of the matrix;

$Q_i$ is the weight fraction of the selected fiber (in g) (expressed as a decimal; e.g., 10%=0.1 g);

π is 3.1417;

$d_i$ is the diameter of the selected fiber (in cm); and $\rho_i$ is the density of the selected fiber (in g/cm³), and where the diameter of the cellulose acetate fibrets is derived according to the following equation:

$$d = \frac{4}{\rho} \times \frac{1}{A/W}$$

where:

d is the diameter of the cellulose acetate fibrets (in cm, or, by multiplying cm by 10,000, in microns);

ρ is the density of the cellulose acetate from which the fibrets are formed (in g/cm³); and A/W is the area-to-weight ratio of the cellulose acetate fibrets (in cm²/g), and (3) deriving the number average diameter (in cm) of all fibers present in the matrix by adding together, for each fiber, the product of the length $L_i$ (in cm) and diameter (in cm) divided by the length $L_i$ (in cm) for each fiber, using the following equation:

$$\frac{\Sigma L_i \times d_i}{\Sigma L_i}$$

(4) observing a selected performance characteristic of the filtration matrix, (5) repeating steps (1) to (4) with different matrixes of the polyester fibers, fiberglass fibers, and cellulose acetate fibers, each matrix selected to create a different number average diameter of the polyester fibers, fiberglass fibers, and cellulose acetate fibers, and (6) expressing change in the selected performance characteristic as a function of change in number average diameter of the polyester fibers, fiberglass fibers, and cellulose acetate fibers present in the filtration media matrixes.

4. A method according to claim 3 wherein, in step (2) length $L_i$ is expressed as a ratio based upon the shortest absolute fiber length present in the matrix by dividing each fiber length by the length of the shortest fiber present, $L_i$ being thereafter expressed in terms of cm per cm of the shortest fiber present.

5. A method according to claim 3 wherein, the manufacturing step includes arranging the media in continuous layers having an overall thickness of greater than 6 mm but not more than about 10 mm, and integrally sealing the layers together about their peripheries.

* * * * *